United States Patent [19]

Noguchi et al.

[11] Patent Number: 4,933,323

[45] Date of Patent: Jun. 12, 1990

[54] NOVEL PEPTIDE AND SALTS THEREOF AND PEPTIDE ANTIALLERGIC AGENTS CONTAINING THESE PEPTIDES

[75] Inventors: Keiichi Noguchi; Daisuke Irie; Bunichiro Nakajima, all of Hitachi, Japan

[73] Assignee: Hitachi Chemical Co., Ltd., Tokyo, Japan

[21] Appl. No.: 315,285

[22] Filed: Feb. 24, 1989

[30] Foreign Application Priority Data

Mar. 28, 1988 [JP] Japan .................................. 63-72011
Sep. 2, 1988 [JP] Japan ................................. 63-218267

[51] Int. Cl.$^5$ ........................ A61K 37/02; C07K 7/06
[52] U.S. Cl. ..................................... 514/17; 530/330
[58] Field of Search ........................... 514/17; 530/380

[56] References Cited

U.S. PATENT DOCUMENTS

| | | | |
|---|---|---|---|
| 4,161,522 | 7/1979 | Hamburger | 530/330 |
| 4,171,299 | 2/1979 | Hamburger | 260/1125 R |
| 4,278,596 | 7/1981 | Garsky | 530/330 |
| 4,552,866 | 11/1985 | Delaney et al. | 514/17 |
| 4,554,101 | 11/1985 | Hopp | 514/17 |
| 4,579,840 | 4/1986 | Hahn | 530/330 |
| 4,585,587 | 4/1986 | Goldberg et al. | 530/330 |
| 4,628,045 | 12/1986 | Hahn | 514/17 |

*Primary Examiner*—Lester L. Lee
*Attorney, Agent, or Firm*—Abelman Frayne Rezac & Schwab

[57] ABSTRACT

Novel peptide having the primary structure Asp-Ser-Asp-Gly-Lys or pharmaceutically acceptable salts thereof.

The present peptide possesses activity of inhibiting histamine release and IgE antibody production in the onset of type I-allergy and is effective in the prevention or therapy of type I-allergias such as bronchial asthma, urticaria and allergic rhinitis.

3 Claims, 4 Drawing Sheets

NOVEL PEPTIDE AND SALTS THEREOF AND PEPTIDE ANTIALLERGIC AGENTS CONTAINING THESE PEPTIDES

BACKGROUND OF THE INVENTION

1. Field of the Invention

The present invention relates to a novel physiologically active peptide and salts thereof, and to antiallergic agents containing the same as an active ingredient. Furthermore, it is concerned with a method for the prevention or therapy of allergies.

2. Description of Prior Art

A variety of drugs have been proposed and developed for the prevention or therapy of various allergic diseases. Some of them have already been placed on the market.

Among the allergic symptoms, immediate-type allergic reactions such as bronchial asthma, urticaria and allergic rhinitis are classified as type I-allergic reaction. The type I-allergic reaction is in general believed on the basis of onset of the symptoms and action mechanism of the antiallergic agent to involve the following three stages: against an extraneous antigen which has entered the body produces IgE antibody, which is fixed to the Fc receptor in tissue mast cells or blood basophils thereby producing sensitization (this process is at the first stage); next, when the extraneous antigen again enters the body, the IgE antibody fixed to the Fc receptor in the cells and the extraneous antigen are bonded to cause antigen-antibody reaction which triggers such reactions as activation of the cell membrane enzymes and inflow of calcium ions into cells thereby producing biochemical changes such as enzymatic reactions and histological changes such as degranulation with a result that chemical mediators such as histamine and SRS-A are released outside the cells (this process is at the second stage); the chemical mediators released outside the cells as mentioned above have such actions as contraction of smooth muscles and accentuation of permeability and promotion of excretion of the capillary blood vessels and cause various allergic symptoms (this process is at the third stage).

Among heretofore known antiallergic agents, non-specific hyposensitization therapeutic agents and antibody production inhibitory agents are drugs acting on the first stage. None of the drugs specifically acting on the first stage has been placed on the market. As drugs acting on the second stage are known chemical mediator-inhibitory agents such as disodium cromoglycate (DSCG) and Tranilast. Antihistaminics and bronchodilators are drugs acting on the third stage. Japanse Patent Publication Sho No. 60-2318 discloses peptide antiallergic agents though not placed on the market. Whereas the peptide has not yet been demonstrated for inhibition of the IgE antibody production at the first stage, it blocks allergic reaction by inhibiting bond of the IgE antibody with mast cells which first occurs at the second stage, as well as by simultaneously substituting the IgE antibody already bonded at the second stage. It is composed of five amino acid residues in Fc region of IgE antibody and, as shown below by the primary structure, is a pentapeptide of IgE antibody origin.

Asp-Ser-Asp-Pro-Arg

Although the peptide is under investigation and development as a pharmaceutical preparation, its level of the activity is not clear.

Based on the mechanism of the onset of allergic symptoms in the type I-allergic reaction, development of antiallergic agents has heretofore been directed to a drug acting on one of the three stages for the onset of allergic symptoms. Studies were made of prevention of onset or therapeutic treatment of allergic symptoms by blocking at any one stage in the chain of the three stages. Therapy which is expected to produce some efficacy has been developed by the development of drugs acting on one of the three stages in the onset of allergic symptoms.

These chemotherapeutic agents, however, cannot completely block the chain of the above-mentioned three stages. Thus, use of a combination of several drugs has been adopted based on an idea of realizing complete blocking of the chain by combined use of a drug acting on one of the three stages with a drug acting on another, but the results are not as expected.

Then, it is expected that development of a drug acting on plural stages of the three stages in the onset of allergic symptoms would drastically improve the effects as an antiallergic agent, and development of such drugs is desirable.

It is also conceivable on the basis of mechanism of the onset of allergic symptoms that superior antiallergic agents would become available if a peptide of IgE antibody origin or a peptide analogous to such peptide is developed. Development of novel peptides by the above-mentioned approach is also expected.

SUMMARY OF THE INVENTION

Under such circumstances, an attempt was made by us of a new design of derivatives related to pentapeptides of IgE antibody origin for the development of pentapeptides with a higher activity.

We designed a new pentapeptide having the primary structure

Asp-Ser-Asp-Gly-Lys and made investigations of its inhibitory activities on the release of chemical transmitters. As a result, we have found that the pentapeptide exerts an activity higher than that of the pentapeptide of IgE antibody origin specifically in inhibition of histamine release.

Surprisingly, the novel pentapeptide also possesses an activity of inhibiting IgE antibody production in addition to the above-mentioned activity of inhibiting histamine release.

The present invention accordingly relates to a novel physiologically active peptide having the primary structure Asp-Ser-Asp-Gly-Lys and pharmaceutically acceptable salts thereof which have an activity of inhibiting the IgE antibody production simultaneously with an activity of inhibiting the histamine release, as well as antiallergic agents containing the same as an active ingredient.

BRIEF DESCRIPTION OF THE DRAWINGS

In FIG. 5 the portion with slashed lines indicates the antibody titer in heat-treated serum. In FIGS. 4 and 5 the vertical axis respectively represents the antibody titer and the horizontal axis represents dose (mg/kg) of the present compound and the control.

DETAILED DESCRIPTION OF THE INVENTION

Figure 1:
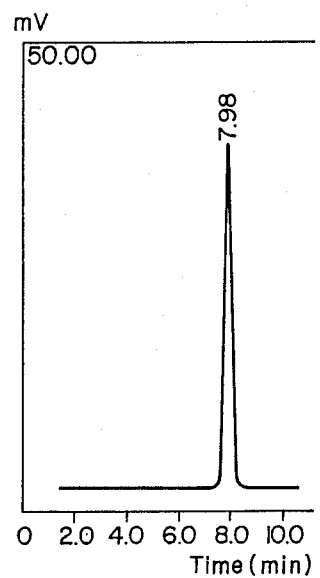
FIG. 1 indicates results of an analysis by high performance liquid chromatography of the novel peptide of the invention in which the vertical axis represents the intensity of ultraviolet absorption at 210 nm and the horizontal axis represents the elution time (minute).

According to the present invention there are provided a novel peptide having the primary structure Asp-Ser-Asp-Gly-Lys or pharmaceutically acceptable salts thereof.

Further, according to the invention there are provided antiallergic agents containing as an active ingredient the above-mentioned peptide or a pharmaceutically acceptable salt thereof.

The invention also provides a method for the prevention or therapy of allergies which comprises administering to patients with allergic diseases an effective dose of the above-mentioned peptide or a pharmaceutically acceptable salt thereof.

The present invention covers pharmaceutical preparations comprising the present compound or a medicinally acceptable salt thereof together with pharmaceutically acceptable carriers or diluents. Preferable examples of the salts include salts with an alkali metal such as sodium or potassium and salts with a metal such as an alkali earth metal, for example, calcium or magnesium, ammonium salts, salts with an organic base, salts with an organic acid and salts with an inorganic acid. The present preparations may be formulated so that the active ingredient is released rapidly, continuously or sustainedly following administration to patients.

The antiallergic agents according to the invention may appropriately be in the form either for oral administration or for parenteral administration. They can be administered by various routes typical of which are oral, rectal, cutaneous, subcutaneous, intravenous, intramuscular, inhalative and nasal ones.

The antiallergic agents of the invention can be administered in various forms of pharmaceutical preparations by the various routes. As these pharmaceutical preparations are mentioned tablet, hard capsule, soft capsule, granule, powder, troche, suppository, syrup, cream, ointment, cataplasma, injection, suspension, inhalation, aerosol and the like. They may also be formed into bilayer tablet or multilayer tablet together with other antiallergic agents and drugs. The tablet can further be coated, as needed, by a conventional method to prepare sugar coated tablet or enteric coating tablet, for example.

In forming solid preparations such as tablet, granule and powder, known additives such as lactose, sucrose, glucose, crystalline cellulose, corn starch, calcium phosphate, sorbitol, glycin, carboxymethylcellulose, hydroxypropylcellulose, gum arabic, polyvinylpyrrolidone, polyethylene glycol, magnesium stearate and talc may be added.

In producing semi-solid preparations such materials as vegetable wax, microcrystalline wax and fat, for example, tallow or lanolin may be added.

In preparing liquid preparations such materials as sodium chloride, sorbitol, glycerin, olive oil, armond oil, propylene glycol, and ethylene glycol may be added.

Dosage of the present compound is 0.01–10 mg/kg/day in oral administration, 0.1–100 mg per shot in nasal administration and 10–1,000 µg/kg/day in parenteral administration, although it may appropriately be increased on decreased depending upon age, bodyweight and symptom of the patient.

The substance of the invention which is a novel peptide having a primary structure Asp-Ser-Asp-Gly-Lys was newly designed by the reasons given below. First, Pro of the C terminal Pro-Arg of the above-mentioned Asp-Ser-Asp-Pro-Arg was substituted with Gly which is a neutral amino acid in the same category. Then, the basic amino acid Arg was replaced by Lys which is a most homologous one.

The substance of the invention produces a single peak by reverse phase HPLC (ODS column, YMA-D-ODS, 20 mm×250 mm) with solvents of the gradient 0.1% TFA→70% CH$_3$CN. The composition is confirmed by the peptide map after enzymatic degradation and the analysis of amino acid after hydrolysis.

The present substance can be prepared either in solid phase or in liquid phase by a conventional method. For example, according to a solid phase technique generally called the Merrifield method, the preparation can be effected as described below by means of the synthesizer Model 990B manufactured by Beckman.

First, a C terminal amino acid of the present substance protected with tertiary butoxycarbonyl group (called Boc for short) at the N terminal is fixed on a chloromethyl resin carrier through an amide bond or an ester bond. More particularly, for example, chloromethyl resin is coupled with Boc-Lys[Z(2Cl)], Boc-Gly, Boc-Asp(OBzl) or Boc-Ser(Bzl). The Boc is then eliminated with an acid. The resin is coupled with an amino acid second to the C terminal in which the N terminal and, if necessary, a functional group of the side chain of the amino acid have in advance been protected to form a peptide. In this reaction, the protected amino acid employed is in an amount of 3–5 times of the theoretical amount, and dicyclohexylcarbodiimide (called DCC for short) is used as a coupling reagent. End point of the reaction is confirmed when reaction of the amino group with ninhydrin becomes negative. Amino acids in which N terminal and, if necessary, a functional group of the side chain of the amino acids are protected are successively reacted in the order of amino acid sequence in the primary structure of the present substance finally to give the present substance with functional groups and N terminal protected. Finally, the resulting substance is treated with hydrofluoric acid to eliminate the protective group and to be released from the resin. In order to prevent side reactions anisole is added in the final treatment. The crude product obtained by removing the hydrofluoric acid may be purified by ion exchange column chromatography. Purity is confirmed by high performance liquid chromatography. If necessary, further purification by preparative high performance liquid chromatography can produce the present substance in pure form. Confirmation of the structure and purity of the present substance could be carried out by means of high performance liquid chromatography, peptide map, amino acid analysis and others.

The present invention is directed to a novel pentapeptide derived from the pentapeptide corresponding to Fc region of IgE antibody, which specifically inhibits the histamine release on the basis of IgE antibody. The novel pentapeptide also inhibits production of the IgE antibody, a factor causing allergy. It is therefore expected that the novel pentapeptide is useful as a therapeutic agent for preventing or curing allergic diseases caused not only by release of chemical transmitters such as histamine but also by increase in the IgE antibody. These two aspects of action possessed by the novel pentapeptide may result in blocking two of the three stages of the chain in the onset of type I-allergic reactions without combined use of plural drugs. Since components of the novel pentapeptide is natural amino acids, the product will easily be metabolized in the body with high safety associated.

The present invention will be described in particulars with reference to an example given below.

EXAMPLE

In the reaction tank of a peptide synthesizer Model 990B manufactured by Beckman is placed 1.50 g of Boc-Lys[Z(2Cl)]-chloromethyl resin [containing 0.33 mmol/g of Boc-Lys[Z(2Cl)], manufactured by Vaga Boichem], which is stirred in $CH_2Cl_2$ for 2 hours to swell.

Then, the next component Boc-Gly is reacted by stepwise procedures as set forth below.

(1) Wash with 20 ml of $CH_2Cl_2$ for 2 min./three times.
(2) Wash with 20 ml of MeOH for 2 min./three times.
(3) Wash with 20 ml of $CH_2Cl_2$ for 2 min./three times.
(4) Wash with 20 ml of 45% TFA and $CH_2Cl_2$ for 5 min./once.
(5) Wash with 20 ml of 45% TFA and $CH_2Cl_2$ for 15 min./once.
(6) Wash with 20 ml of $CH_2Cl_2$ for 2 min./three times.
(7) Wash with 20 ml of MeOH for 2 min./three times.
(8) Wash with 20 ml of $CH_2Cl_2$ for 2 min./three times.

At this point, positive amino group reaction is confirmed with ninhydrin.

(9) Wash with 20 ml of 10% TFA and $CH_2Cl_2$ for 2 min./once.
(10) Wash with 20 ml of $CH_2Cl_2$ for 2 min./three times.
(11) Dissolve 4 equivalents of a Boc-protected amino acid and 10 ml of $CH_2Cl_2$ in a mixed solution of 2 equivalents of DCC and 5 ml of $CH_2Cl_2$, add the solution and then shake in ice water for 20 min. to effect the reaction. Dry precipitates thus produced followed by suction filtration on a glass filter to obtain a Boc-amino acid anhydride.
(12) Wash with 20 ml of $CH_2Cl_2$ for 2 min./three times and confirm negative amino group reaction with ninhydrin.
(13) Wash with 20 ml of MeOH for 2 min./three times.
(14) Wash with 20 ml of $CH_2Cl_2$ for 2 min./three times.

Introduction of Boc-Gly is completed by the above procedures.

Subsequently, the steps (1) to (14) are repeated successively for Gly through the N terminal. The protected amino acids are added in the order shown below.
Boc-Asp(OBzl): 1.50 g,
Boc-Ser(OBzl): 1.50 g,
Boc-Asp(OBzl): 1.50 g.

Completion of the above procedures results in synthesis of the protected peptide
Boc-Asp(OBzl)-Ser(Bzl)-Asp(OBzl)-Gly-Lys[Z(2Cl)]-resin.

The protected peptide on the resin is filtered off after the above-described steps (1)–(14) conducted and dried overnight in a desiccator. There is obtained 1.94 g of the dried protected peptide-resin. It is treated with 30 ml of hydrofluoric acid in the presence of 2 ml of anisole and 0.5 ml of DMS at 0° C. for 1 hour. The hydrofluoric acid is distilled off, and the residue is washed with anhydrous ether-n-hexane (1:1) mixture and then with anhydrous ether alone and thoroughly dried. The peptide is dissolved in 50 ml of 10% acetic acid, and undissolved resin is filtered off.

The solution thus obtained is placed on a Dowex I-X2 column (1×15 cm) followed by elution with 2N acetic acid. The solution thus produced is filtered through a 0.22μ milipore filter and freeze dried. There is obtained 360 mg of a crude peptide. It is further subjected to high performance liquid chromatography under the conditions:

Column: YMC-D-ODS 20 mm×250 mm
Solvent: Solvent composed of 0.1% TFA and $CH_3CN$ mixed in a proportion with a gradient from 0% to 70%
Flow rate: 1.0 ml/min.

By said high performance liquid chromatography is produced 46.8 mg of a pure peptide with a purity of 97%. This corresponds to a yield of 13%. The pure peptide thus obtained are measured for peptide map and amino acid analytical value and are confirmed to be the present substance. Codes for the description are:
Z(2Cl): 2-chlorobenzyloxycarbonyl
Bzl: Benzyl.

Results of analysis of high performance liquid chromatography carried out for the novel peptide of the invention under separation conditions given below are shown in FIG. 1.
Eluent: 0.1% TFA-$H_2O$
Flow rate: 1 ml/min.
Detection: 210 nm
Column: YMC R-ODS (4.6 mm×250 mm).

Figure 2:
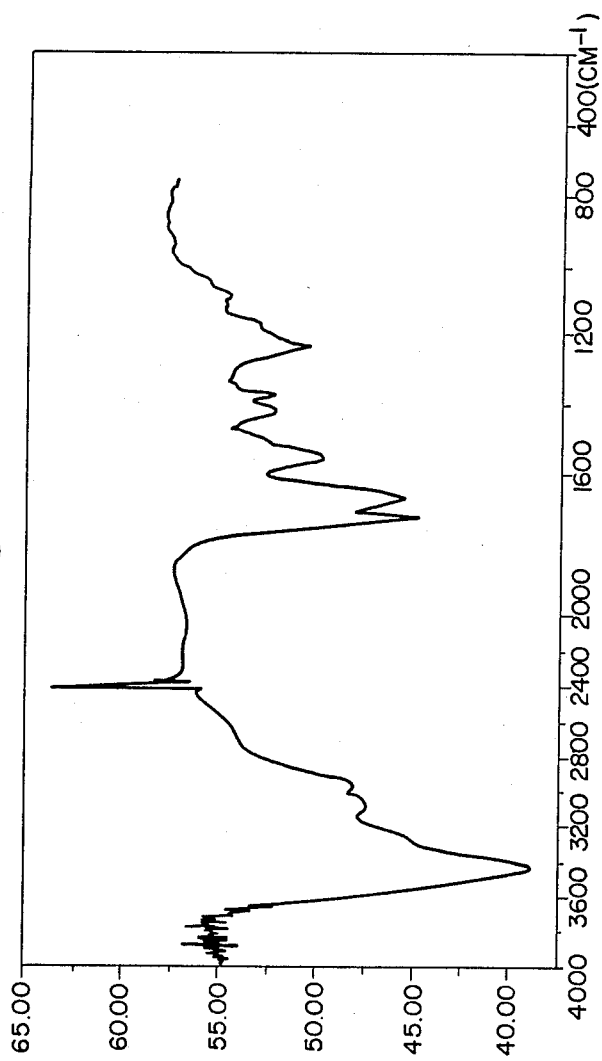
FIG. 2 indicates an infrared absorption spectrum of the present compound.

The infrared absorption spectrum is shown in FIG. 2.

The novel peptide of the invention has characteristic physical properties:
Hydrophobity (Hφ): 1.86
Molecular weight: 520.6
Isoelectric point: 3.7

Results of amino acid analysis carried out for the product of the example are shown below for reference.

After a hydrolysis reaction in 6N HCl (containing 0.1% phenol) at 110° C. for 24 hours, analysis was made using a Hitachi amino acid analyzer model 835. As shown below experimental values well corresponded to the theoretical values to establish that the produce was the desired substance according to the invention.

| Amino acid | Theoretical value | Experimental value |
| --- | --- | --- |
| Asp | 2.0 | 2.0 |
| Ser | 1.0 | 1.0 |
| Gly | 1.0 | 1.1 |
| Lys | 1.0 | 1.0 |

Effect of the invention will be shown below with reference to test examples.

TEST EXAMPLE 1

Inhibitory activity on histamine release from mast cells was tested to investigate antiallergic action of the compound of the invention.

Method

Male Wistar rats weighing 300–350 g were passively sensitized, intraperitoneal mast cells of which were then employed. Rat antiserum for use in the passive sensitization were prepared in accordance with the method of Mota [Immunology, 7 p. 681 (1964)] and the method of Hamaoka [J. Immunology, 113, p. 958 (1974)]. Male Wistar rats (weighing 200–250 g) were each injected with eggwhite albumin (10 mg/kg) intramuscularly on the both thighs in a volume of 5 ml/kg simultaneously with intraperitoneal administration of $2 \times 10^{10}$ cells of killed *Bordetella pertussis* for immunization. Blood was drawn from the abdominal aorta under ether anesthesia on the 12th day of the initial sensitization, and antiserum was separated. The antiserum was lyophilized and stored at $-20°$ C. Titer of the antiserum was measured by the 48 hr. rate PCA reaction. The antiserum with a titer multiplied 128–256 fold was placed for the experiment. The eggwhite albumin rat IgE serum was diluted two fold, and 1 ml of the diluted serum was intraperitoneally administered for sensitization. The rat was blooded to death 48 hrs. after the sensitization, and 15 ml of a phosphate buffer solution (8 g of NaCl, 0.2 g of KCl, 2.88 g of $Na_2HPO_4.12H_2O$, 0.2 g of $KH_2PO_4$, 0.2 g of EDTA 2 Na and 1 g of bovine serum albumin dissolved in purified water to 1 lit., pH 7.4, called PBS (−) for short hereinbelow) was intraperitoneally injected. The rat was then given light abdominal massage for ca. 2 min. and subjected to laparotomy to collect cells in the abdominal cavity. The cell suspension was centrifuged (1,000 rpm, 10 min.) and then resuspended in BPS (−). The BPS (−) suspension was overlayered upon gum arabic density (specific gravity 1.075) followed by centrifugal separation (2,500 rpm, 10 min.). Deposited cells were washed twice with BPS (−) and suspended in fresh PBS [solution in which the EDTA 2 Na in PBS (−) is replaced by 0.1 g of $CaCl_2$, called BPS (+) for short] and adjusted to $1 \times 10^5$ cells/ml. The cell suspension was divided in a volume of 0.8 ml per tube into silicon-treated test tubes, which were then preincubated at 37° C. for 10 min. In the test tube containing the cell suspension was placed 0.1 ml of the test solution with a concentration adjusted with PBS (+) followed by incubation at 37° C for 15 min. To the test tube was then added 0.1 ml of a mixed solution of eggwhite albumin antigen (final concentration 1 mg/ml) and phosphatidyl-L-serine (final concentration 100 μg/ml) followed by incubation for additional 15 min. to suspend the histamine from mast cells. DSCG was added 30 sec. prior to the addition of antigen. After addition of the antigen, incubation was made for additional 15 min. Then, 1 ml of ice-cooled PBS (+) was added to terminate the reaction followed by centrifugal separation at 2,500 rpm for 10 min. To 2 ml of the supernatant was added 1 ml of 4% solution of perchloric acid for use as the sample for the determination of free histamine. For total histamine, 0.8 ml of an untreated mast cell suspension ($1 \times 10^5$ cells/ml) was placed in boiling water for 10 min. followed by addition of 4% perchloric acid to prepare the sample for the determination of total histamine.

Histamine in each sample was measured by fluorimetry, and ratio of histamine release (%) was calculated by the following equation:

Ratio of histamine release (%) =

$$\frac{\text{Amount of free histamine}}{\text{Amount of total histamine}} \times 100$$

Results

Figure 3:
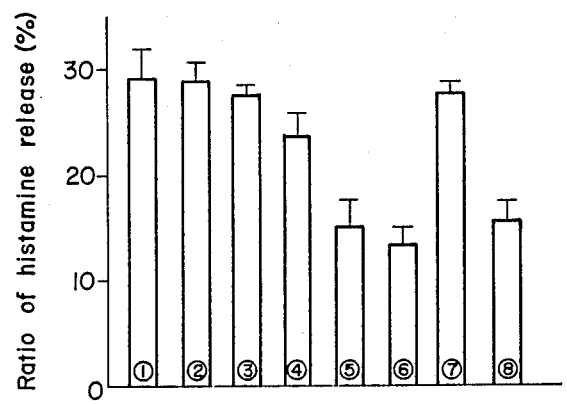
FIG. 3 is a graph indicating the ratio of histamine release (%) caused by the present compound, in which the vertical axis represents the ratio of histamine release (%) and the horizontal axis represents the molar concentration of the present compound or a control substance.

Ratio of histamine release (%) at each concentration of the present compound was shown in FIG. 3 of the attached drawing. As clearly seen from FIG. 3, the present compound exerted an inhibitory action on histamine release at a concentration of $10^{-6}$ M. The potency was approximately equal to or higher than that of DSCG.

TEST EXAMPLE 2

Inhibitory activity on IgE antibody production was tested in mice in order to investigate antiallergic action of the present compound.

Method

Groups of five male BALB/c mice (20–25 g) were used as the immunized animal. An antigen, 10 μg of DNP-BSA was adsorbed on 4 mg of aluminum hydroxide gel, an immunoenhancer. Experiments were carried out by the method described below.

In Test 2-1, 1 mg and 10 mg of the present compound respectively were intraperitoneally given, 30 min. later the DNP-BSA was intraperitoneally administered and on the 14th day blood was drawn to obtain serum.

In Test 2-2, the DNP-BSA was intraperitoneally administered and on the 13th day, 1 mg and 10 mg of the present compound respectively were intraperitoneally given. On the next day the animal was again immunized with the DNP-BSA, and on the 14th day of the immunization blood was drawn to obtain serum.

Antibody titer was measured by the rat 48 hr. PCA reaction for the serum obtained in Tests 2-1 and 2-2.

In particulars, male Wistar rats (200–250 g) were sensitized with the serum subcutaneously on the back, and 48 hrs. later DNP-BSA solution containing 0.5% Evans blue was intravenously injected on the tail. Antibody titer was measured after 30 min. by developed pigment spot. In order to confirm that the antibody titer as obtained by the PCA reaction is for IgE, the serum was heat-treated at 56° C. for 3 hrs., in addition to the untreated run, and antibody titer was measured by the PCA reaction.

Results

Figure 4:
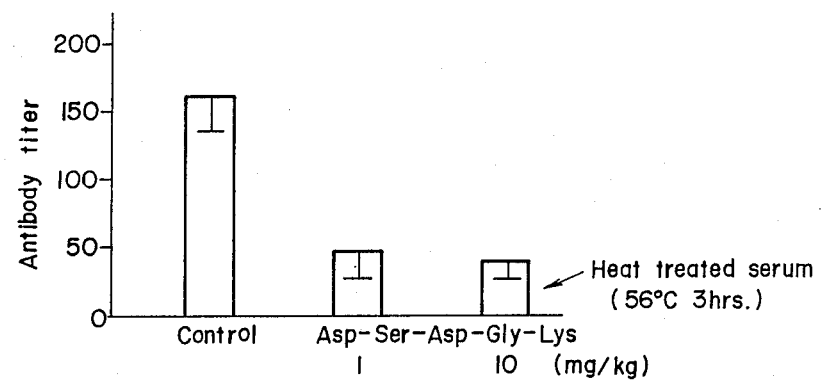
FIG. 4 is a graph indicating the activity of IgE antibody produced by pretreatment with the present compound.
Figure 5:
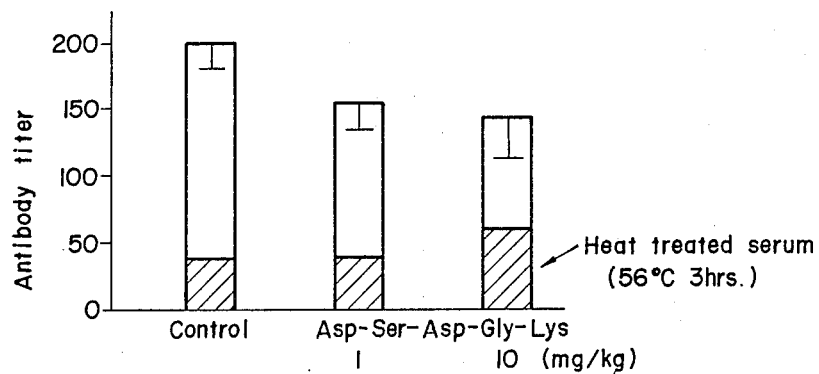
FIG. 5 is a graph indicating the activity of IgE antibody produced when administered during duration of IgE antibody production.

IgE antibody production at each concentration of the present compound was shown in FIG. 4 and FIG. 5 of the attached drawing in terms of the antibody titer determined by the PCA reaction. As clearly seen from FIG. 4 and FIG. 5, the present compound strongly inhibited IgE antibody production at concentrations of 1 mg and 10 mg, respectively. The antibody titer of the heat-treated serum was 0 for the serum in Test 2-1 (FIG. 4) but was slightly positive for the serum in Test 2-2 as shown in FIG. 5 (slashed lines).

What is claimed is:
1. A novel pentapeptide having the primary structure Asp-Ser-Asp-Gly-Lys or pharmaceutically acceptable salts thereof.
2. An antiallergic agent containing as an effective component the peptide or a pharmaceutically acceptable salt thereof according to claim 1 together with the pharmaceutically acceptable carriers or diluents.
3. A method for the prevention or therapy of allergies which comprises administering to a person an effective dose of the peptide or a pharmaceutically acceptable salt thereof according to claim 1.

* * * * *